US011495067B2

(12) United States Patent
Mirkar et al.

(10) Patent No.: US 11,495,067 B2
(45) Date of Patent: Nov. 8, 2022

(54) SECURITY SYSTEM WITH TEMPERATURE SENSING (71) Applicant: Johnson Controls Tyco IP Holdings LLP, Milwaukee, WI (US)

(72) Inventors: Nikhil D. Mirkar, Vashi (IN); Manali V. Pednekar, Thane West (IN)

(73) Assignee: Johnson Controls Tyco IP Holdings LLP, Milwaukee, WI (US)

( * ) Notice: Subject to any disclaimer, the term of this patent is extended or adjusted under 35 U.S.C. 154(b) by 0 days.

(21) Appl. No.: 17/145,032

(22) Filed: Jan. 8, 2021

(65) Prior Publication Data

US 2022/0051497 A1 Feb. 17, 2022

Related U.S. Application Data (60) Provisional application No. 63/065,737, filed on Aug. 14, 2020, provisional application No. 63/065,742, filed on Aug. 14, 2020.

(51) Int. Cl.
*G05B 19/00* (2006.01)
*G07C 9/00* (2020.01)
(Continued)

(52) U.S. Cl.
CPC ........ *G07C 9/00182* (2013.01); *A61B 5/0008* (2013.01); *A61B 5/0075* (2013.01); *A61B 5/01* (2013.01); *A61B 5/6897* (2013.01); *A61B 5/7282* (2013.01); *A61B 5/746* (2013.01); *A61L 2/10* (2013.01); *A61L 2/24* (2013.01); *G01J 5/58* (2013.01); *G05B 15/02* (2013.01); *G06K 7/10297* (2013.01); *G07C 9/00563* (2013.01); *G08B 21/182* (2013.01); *H04L 67/12* (2013.01); *A61L 2202/11* (2013.01); *A61L 2202/14* (2013.01); *G06V 40/13* (2022.01); *G06V 40/19* (2022.01)

(58) Field of Classification Search
CPC ... G07C 9/00563; G01J 5/58; G06K 7/10297; G06K 9/00013; G06K 9/00604; G08B 21/182; A61B 5/01
USPC ...................................................... 340/5.53
See application file for complete search history.

(56) References Cited

U.S. PATENT DOCUMENTS

| 10,847,009 | B1 * | 11/2020 | Sulucz | ................. G08B 17/125 |
| 2007/0213877 | A1 * | 9/2007 | Hart | ........................ G07C 9/22 700/282 |

(Continued)

*Primary Examiner* — Zhen Y Wu
(74) *Attorney, Agent, or Firm* — ArentFox Schiff LLP (57) ABSTRACT

An access control system includes an identification unit having an infrared (IR) transmitter that transmits IR radiation, an IR detector that receives the reflected IR radiation from one or more body parts of the user, one or more signal processing components to determine a temperature of the user based on the received reflected IR radiation, and an identification device to receive identification information of the user. The access control system also includes a processor that receives the reading of the user, instructs a door lock controller to unlock a door when the temperature is below the threshold temperature or the temperature is within the temperature range. The processor sends an alert when the temperature is above the threshold temperature or the temperature is outside the temperature range, and sends identification information of the user to one or more network devices.

14 Claims, 7 Drawing Sheets

(51) Int. Cl.
*G05B 15/02* (2006.01)
*A61B 5/00* (2006.01)
*A61B 5/01* (2006.01)
*A61L 2/24* (2006.01)
*A61L 2/10* (2006.01)
*G08B 21/18* (2006.01)
*H04L 67/12* (2022.01)
*G01J 5/58* (2022.01)
*G06K 7/10* (2006.01)
*G06V 40/13* (2022.01)
*G06V 40/19* (2022.01)

(56) References Cited

U.S. PATENT DOCUMENTS

| | | | |
|---|---|---|---|
| 2008/0180211 A1* | 7/2008 | Lien | G07C 9/00309 |
| | | | 340/5.61 |
| 2016/0210624 A1* | 7/2016 | Niu | G06F 21/32 |
| 2016/0249748 A1* | 9/2016 | Winters | G08B 21/02 |
| | | | 340/4.34 |
| 2018/0211461 A1* | 7/2018 | Xin | G07C 9/00563 |
| 2019/0192010 A1* | 6/2019 | Mane | A61B 5/165 |
| 2020/0006988 A1* | 1/2020 | Leabman | H05B 3/34 |
| 2020/0294245 A1* | 9/2020 | Oyaizu | G06V 40/103 |
| 2021/0056786 A1* | 2/2021 | De La Garza | H04L 67/12 |
| 2021/0345885 A1* | 11/2021 | Umeda | A61B 5/02055 |
| 2021/0383099 A1* | 12/2021 | Oberholzer | G06V 40/172 |

\* cited by examiner

SECURITY SYSTEM WITH TEMPERATURE SENSING

CROSS-REFERENCE TO RELATED APPLICATIONS

This application claims priority to U.S. Provisional Patent Application 63/065,742 titled "SECURITY SYSTEM WITH TEMPERATURE SENSING" filed on Aug. 14, 2020 and U.S. Provisional Patent Application 63/065,737 titled "SECURITY SYSTEM WITH HAND SANITIZATION" filed on Aug. 14, 2020, the disclosures of which are hereby incorporated by reference.

TECHNICAL FIELD

The described aspects relate to access control technologies and specifically to security systems with additional safety features, including temperature sensing.

BACKGROUND

In the context of managing access control, identification and authentication may be achieved based on biometric identification features, however, user specific safety concerns are typically ignored when a determination is made to grant or deny access.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An example implementation includes an access control system for managing access to a secured area. The access control system includes an identification unit, the identification unit including an infrared (IR) transmitter configured to transmit IR radiation to one or more body parts of a user, an IR receiver configured to receive reflected IR radiation from the one or more body parts of the user, one or more signal processing components to determine a temperature measurement of the body of the user based on the received IR radiation, and an identification device to receive identification information of the user. The access control system also includes a processor configured to receive the temperature measurement of the body of the user, determine whether the temperature is below a threshold temperature, or the temperature is within a temperature range, instruct a door lock controller to unlock a door when the temperature is below the threshold temperature or the temperature is within the temperature range, instruct a door lock controller to keep the door in a locked state when the temperature is above the threshold temperature or the temperature is outside the temperature range, and raise an alarm when the temperature is above the threshold temperature or the temperature is outside the temperature range and send identification information of the user to one or more network devices.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

The method and apparatus of the present application may provide one or more additional features to a security system such as an access control system. The access control system of the present disclosure may restrict entry of an individual suffering from an infectious disease based on determining one or more symptoms of the individual. The access control system may further include one or more sanitizing features to sanitize body parts of a user (e.g., hands and/or palms of the user). Thus, the access control system may provide safety and sanitization features in addition to secure and controlled access to an area. The access control system may support on-top integration, i.e., integration with existing/ legacy access control systems (e.g., using a compatible interface) without modification of the existing architecture of the existing/legacy control systems, thereby allowing savings in time and cost in installation and configuration of the access control system and providing an economical solution. The on-top integration of the access control system may also allow easy maintenance of one or more components of the access control system. Further, the on-top integration may enable the one or more components of the access control system to remain in function irrespective of failures at one or more components of the existing control systems.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

Figure 1:
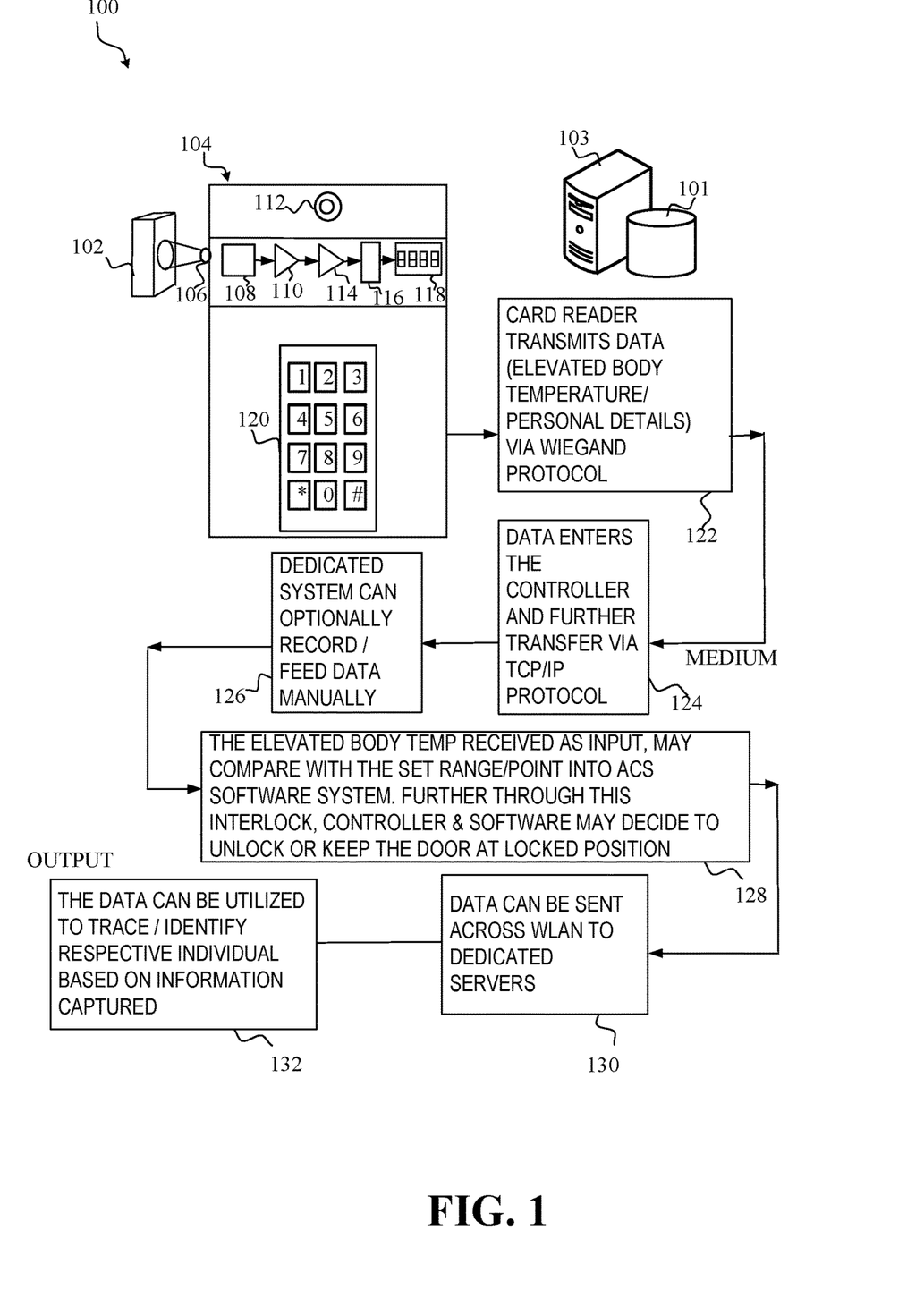
FIG. 1 is a block diagram of a first implementation of an access control system with additional safety features.

Referring to FIG. 1, an access control system 100 for securing an area includes a source reader 104 that may read one or more parameters of a source 102 attempting to gain access to the secured area. In one example, the source 102 may be a user entering a keycode to gain access to the secured area. In another example, the source 102 may be a bar code or an radio frequency identification (RFID) code embedded on a card. The source reader 104 may include a camera 112 that may monitor the source 102 trying to gain access to the secured area. The camera 112 may be connected to one or more components of the access control system 100 to store the video feed or provide live video feed to a security personnel. The source reader 104 may include a keypad 120 that may enable a user trying to gain access to enter their credentials. In one implementation, the source reader 104 may include an RFID card reader or a barcode reader to read credentials of the user stored on a card. The keypad 120 and/or the RFID card reader may be connected to one or more components of the access control system 100 that determine whether the user is to be allowed access to the secured area based on the presented credentials. The source reader 104 may also include a display 118 to indicate to the user the inputs being made through the keypad 120. The display 118 may also indicate to the user whether an access to the secured area is granted or denied.

The source reader 104 may include an light emitting diode (LED) component 106 including one or more LEDs. For example, the LED component 106 may include an LED to provide indication whether an access to the source 102 is granted (e.g., by a green color indication) or the access is denied (e.g., by a red indication). The LED component 106 may include an IR transmitter LED that may act as a source of IR radiation. The source reader 104 may include an IR detector 108 e.g., an IR receiver which may be a photodiode to detect the IR radiation transmitted by the IR transmitter LED. In one implementation, the IR transmitter LED and the IR receiver may be integrated into a card reader unit (e.g., an RFID card reader as described above). The IR transmitter may be positioned to be pointed to the source 102 in such a manner that the transmitted IR radiation is focused on one or more body parts (e.g., forehead) of a user attempting to gain access to the secured area. The IR transmitter may emit rays on the forehead of the user at the time of attempting access to the secured area or entering/displaying credentials. The IR detector 108 may detect the reflected IR radiation from the body parts of the user which may be amplified by an amplifier 110. The amplified signals may be processed by a signal conditioner 114 (e.g., by amplifying, filtering and/or attenuating) the signals received from the amplifier 110 for processing by the analog-to-digital (ADC) converter 116. The ADC converter 116 may convert the received signals to digital signals suitable to be processed by one or more components of the access control system 100 to obtain temperature reading(s) of the user trying to gain access to the secured area. One or more components of the source reader 104 may be integrated with one or more access control components of an existing access control system(s) to support on-top integration with the existing access control system(s). For example, the display 118 may be configurable to receive an input from an authentication component of the existing access control system to output on the display 118 whether a user is allowed access.

A storage device 101, such as any type of memory, of the access control system 100 may store the temperature reading(s) of the user. A processor 103 of the access control system 100 may classify temperature reading(s) of the user to be flashed on to an Alarm/Log Report list of the access control system 100. For example, the processor 103 of the access control system 100 may classify temperature reading(s) of the user to be flashed on the Alarm/Log Report list when the temperature reading(s) of the user are greater than a threshold (e.g., 99.4 degrees Fahrenheit). Further, the processor 103 of the access control system 100 may classify temperature reading(s) of the user on the Alarm/Log Report list in a different color (e.g., green) when the temperature reading(s) of the user are below the threshold, and the processor of the access control system 500 may classify temperature reading(s) of the user on the Alarm/Log Report list in a different color (e.g., red) when the temperature reading(s) of the user are above the threshold. The LED component 106 and the IR detector 108 (which may be built into an RFID card reader) may be installed at facelift height and pointing on forehead at eye level of a user trying to gain access to the secured area.

A security management system of the access control system 100 may provide the data (such as red classified entries in the Alarm/Log Report list) to a log alarm report. The security management system may be defined by instructions executed by the processor 103, and the log alarm report may be stored in the storage device 101. The display 118 may display a pop-up when the temperature of the user captured is above a threshold. Further, the processor of the access control system 100 may sound an audible alarm may be along with displaying the pop-up on the display 118. The camera 112 may be connected to a storage device of the access control system 100 communication network and capture an image(s) and/or video of the person trying to gain access to the secured area via an installed close circuit television (CCTV) and/or a Video Intercom system integrated with the access control system 100. The processor 103 of the access control system 500 may classify image(s) and/or video captured by the camera 112 of a person based on comparison against one or more identifying pictures of users stored in the storage of the access control system 100. On identifying the person based on such comparison and/or the identification details of the person received from the source reader 104, the processor 103 of the access control system 100 may alert a security officer about other details of the person such as: name, contact numbers, addresses, etc. The processor 103 may further send such details to state municipal departments, health departments, traffic signal departments or state police departments in case of a pandemic scenario via the communication network of the access control system 100. Such data may enable limiting, tracing or tracking the movements of the user. The access control system 100 having the keypad 120 and/or the RFID card reader may support on-top integration with enterprise access control systems without modification of their existing architecture, thereby allowing savings in time and cost and providing an economical solution.

Blocks 122-132 further describe the operations in the access control system 100. For example, these operations may be performed by one or more hardware components of the system separately, and/or in conjunction with, the processor 103 executing computer-readable instructions stored in the storage device 101. At block 122, the source reader 104 may send temperature reading(s) of the user (as described above) to the processor 103 of the access control system 100 over network interface (e.g., over a Wiegand interface using Wiegand protocol). At block 124, the processor 103 or a controller of the access control system 100 may receive the data including temperature reading(s) of the user. The processor 103 may transfer/send the data may to one or more devices of the access control system 100 via a communication network of the access control system 100 (e.g., using transmission control protocol (TCP)/internet protocol (IP) (TCP/IP). At block 126, a dedicated system (e.g., a record logging unit of the access control system 100) may record the data. Also, an operator or a security officer may record the data into the dedicated system. At block 128, the processor 103 of the access control system 100 may compare the temperature reading(s) of the user against a threshold temperature value (e.g., 37.5 degrees Celsius (99.5 degrees Fahrenheit)) or a range of temperature values (e.g., 36.5 degrees Celsius (97.7 degrees Fahrenheit)-37.5 degrees Celsius (99.5 degrees Fahrenheit)). In one implementation, on determining that the temperature reading(s) of the user is below the threshold temperature value, the processor 103 may send instructions to a door lock controller to unlock a door to allow the source 102 access to the secured area. In another implementation, on determining that the temperature reading(s) of the user falls outside the range of temperature values, the processor 103 may send instructions to the door lock controller to unlock a door to allow the source 102 access to the secured area. The processor 103 may instruct the door lock controller to keep the door in a locked state when the temperature reading(s) of the user are above the threshold temperature value and/or outside the range of temperature values. Further, the processor 103 may log the temperature values in an Alarm/Log Report (as described above).

At block 130, the processor 103 may send alerts (including details of an identified user as described above) to a security officer and other public health departments when the temperature reading(s) of the user are above the threshold temperature value and/or within the range of temperature values. At block 132, the output data may be utilized by one or more security officers/public health agencies to track, trace and/or limit mobility of the user.

Figure 2:
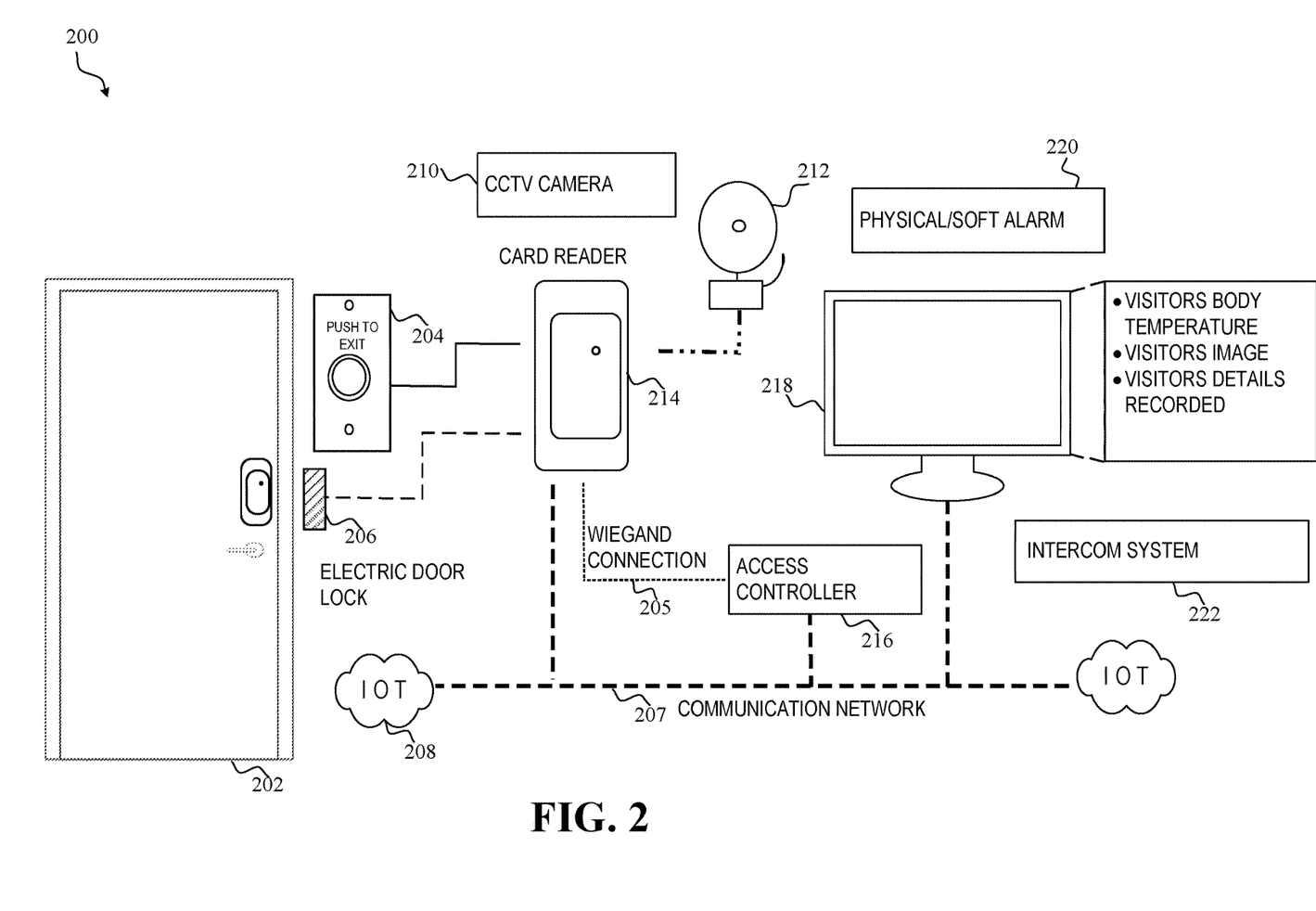
FIG. 2 is a high level diagram of system components of an access control system with additional safety features.

Referring to FIG. 2, a system architecture diagram 200 of the access control system 100 (as described above with reference to FIG. 1), includes an access control door 202 that may provide a controlled access to the source 102. The operations described with respect to FIG. 2 may be performed by one or more hardware components of the system separately, and/or in conjunction with, the processor 103 executing computer-readable instructions stored in the storage device 101. The access control door 202 may include the source reader 104 to allow a user trying to gain access to the controlled area to interact with the access control system 100 and present the credentials of the user. In one implementation, the access control door 202 may include a card reader 214 (similar to a card reader unit as described above in FIG. 1). The card reader 214 may include the IR transmitter LED and the IR detector (as described above in FIG. 1) for obtaining temperature reading(s) of a user. The card reader 214 may be coupled to an access controller 216 via a Wiegand interface/connection 205. The access controller 216 may perform some or all operations of the processor of the access control system 100 (as described above in FIG. 1). The card reader 214 and the access controller 216 may be coupled to one or more internet of things (IOT) devices 208 such as an emergency alert system, one or more servers of public health departments, etc. via a communication network 207 of the access control system 100. The system architecture diagram 200 may include a request to exit button 204 that may allow a user to request exit in case of an unsuccessful authentication.

The system architecture diagram 200 may also include a CCTV camera 210 (similar to the camera 112 as described above in FIG. 1) and an electric door lock 206 that may be selectively unlocked based on instructions received from the access controller 216 (based on determination of the temperature reading(s) of the user as described above in FIG. 1).

The access controller 216 may be coupled to an access control component 218 (which may include access control software, firmware, and/or hardware components, which may be associated with the storage device 101 and/or the processor 103) to perform the operations as described above in FIG. 1. The access controller 216 may also be coupled to a local alarm 212 to immediately alert a security officer managing the secured area when the temperature reading(s) of the user are above the threshold temperature value and/or outside the range of temperature values (as described above in FIG. 1). The access control component 218 may maintain information logs about the user trying to gain access to the secured area such as a body temperature of the user, an image of the user captured via the installed CCTV and/or the Video Intercom system integrated with the access control system 100. The access control component 218 may include a physical/soft alarm 220 that may be triggered when the temperature reading(s) of the user are above the threshold temperature value and/or outside the range of temperature values. The triggering of the physical/soft alarm 220 may cause the access controller 216 to perform one or more operations such as update entries in an Alarm/Log Report. The access controller 216 may be coupled to an intercom system 222 to call a security officer when the physical/soft alarm 220 is triggered.

Figure 3:
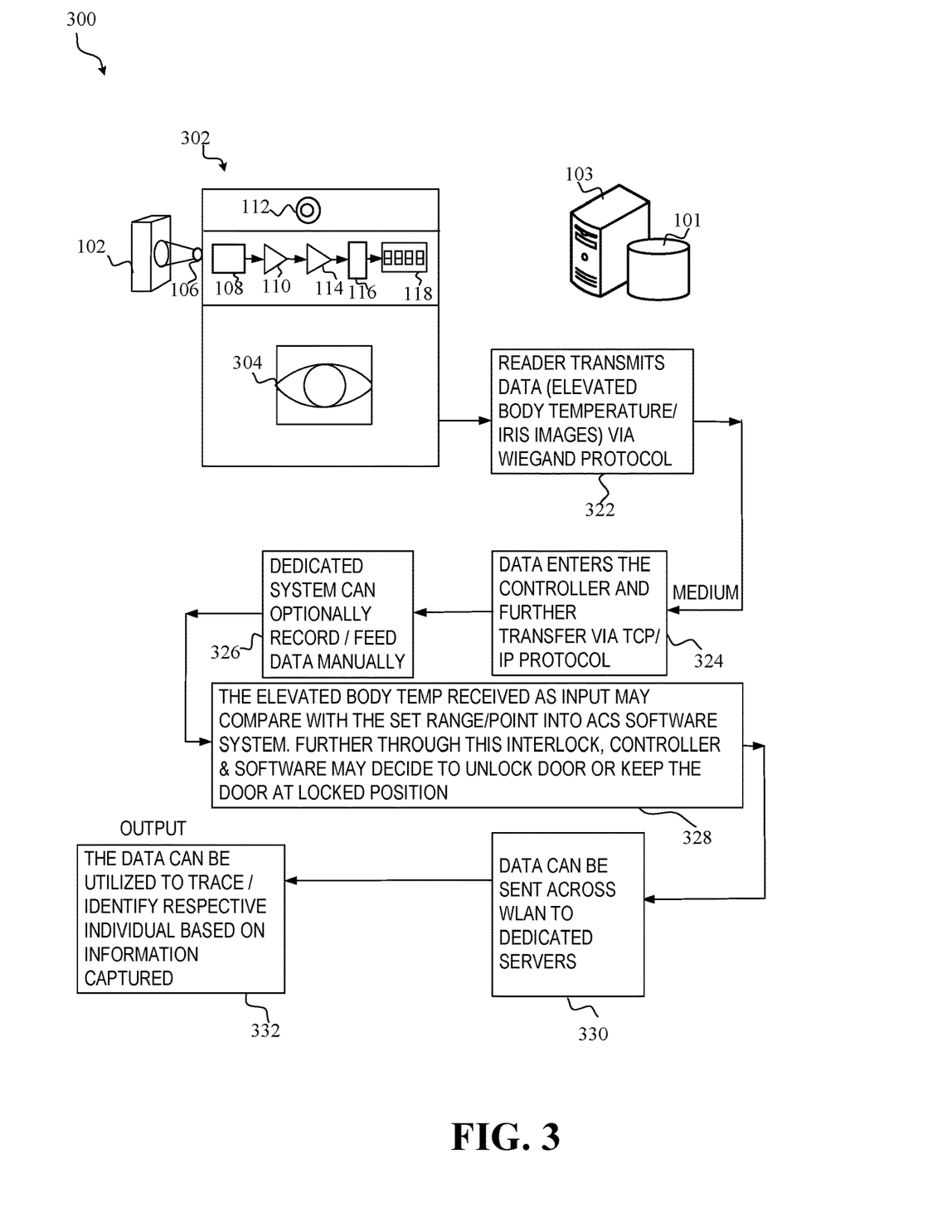
FIG. 3 is a block diagram of a second implementation of an access control system with additional safety features.

Referring to FIG. 3, an access control system 300 includes similar entities as the access control system 100 in FIG. 1 with the biometric identification unit 302 in place of the source reader 104. The biometric identification unit 302 includes the LED component 106, the IR detector 108, the amplifier 110, the signal conditioner 114, the ADC converter 116 and the display 118 (as described above in FIG. 1). The biometric identification unit 302 includes a biometric scanner 304 to scan one or more body parts (e.g., iris, one or more fingers, palm, etc.) of a user trying to gain access to a secured area. In one implementation, the biometric scanner 304 includes an iris scanner as shown in FIG. 3. The biometric scanner 304 may capture the identifying information of the user trying to gain access and send the identifying information to a processor 103 of the access control system 300. The processor 103 may compare the identifying information received from the biometric scanner 304 of the biometric identification unit 302 against one or more allowed user identifier stored in a storage of the access control system 300 to determine whether the user trying to gain access should be granted access.

The biometric identification unit 302 may include the LED component 106 (as described above in FIG. 1) having an IR transmitter LED that may act as a source of IR radiation. The biometric identification unit 302 may include the IR detector 108 (as described above in FIG. 1) e.g., an IR receiver which may be a photodiode to detect the IR radiation. In one implementation, the IR transmitter LED and the IR detector 108 may be integrated into the biometric identification unit 302. The IR transmitter may be positioned to be pointed to the source 102 in such a manner that the transmitted IR radiation is focused on one or more body parts (e.g., forehead) of a user attempting to gain access to the secured area. The IR transmitter may emit rays on the forehead of the user at the time of attempting access to the secured area or entering/displaying credentials. The IR detector 108 may detect the reflected IR radiation from the body parts of the user which may be amplified by an amplifier 110. The signal conditioner 114 may process (e.g., by amplifying, filtering and/or attenuating) the amplified signals received from the amplifier 110 for processing by the ADC converter 116. The ADC converter 116 may convert the received signals to digital signals suitable to be processed by one or more components of the access control system 300 to obtain temperature reading(s) of the user trying to gain access to the secured area.

A storage device 101, such as any type of memory, of the access control system 300 may store the temperature reading(s) of the user. The processor 103 of the access control system 300 may flash the temperature reading(s) of the user on to an Alarm/Log Report list of the access control system 300. For example, the processor 103 of the access control system 300 may classify temperature reading(s) of the user to be flashed on the Alarm/Log Report list when the temperature reading(s) of the user are greater than a threshold (e.g., 99.4 degrees Fahrenheit). Further, the processor 103 of the access control system 300 may classify temperature reading(s) of the user may be classified on the Alarm/Log Report list in a different color (e.g., green) when the temperature reading(s) of the user are below the threshold, and the processor 103 of the access control system 500 may classify temperature reading(s) of the user on the Alarm/Log Report list in a different color (e.g., red) when the temperature reading(s) of the user are above the threshold. The LED component 106 and the IR detector 108 (which may be built into the biometric scanner 304) may be installed at facelift height and pointing on forehead at eye level of a user trying to gain access to the secured area.

A security management system of the access control system 300 may provide the data (such as red classified entries in the Alarm/Log Report list) to a log alarm report. The security management system may be defined by instructions executed by the processor 103, and the log alarm report may be stored in the storage device 101. The display 118 may display a pop-up when the temperature of the user captured is above a threshold. Further, the processor 103 of the access control system 300 may send instructions to sound an audible alarm along with displaying the pop-up on the display 118. The camera 112 may be connected to a storage device of the access control system 300 communication network and capture an image(s) and/or video of the person trying to gain access to the secured area. The processor 103 of the access control system 300 may classify image(s) and/or video captured by the camera 112 of a based on comparison against one or more identifying pictures of users stored in the storage of the access control system 300. On identifying the person based on such comparison and/or using the identification details received from the biometric identification unit 302, the processor 103 of the access control system 300 may alert a security officer about other details of the person such as: name, contact numbers, addresses, etc. The processor 103 may further send such details to state municipal departments, health departments, traffic signal departments or state police departments in case of a pandemic scenario via the communication network of the access control system 300. Such data may enable limiting, tracing or tracking the movements of the user. The access control system 300 having the biometric scanner 304 may support on-top integration with enterprise access control systems without modification of their existing architecture, thereby allowing savings in time and cost and providing an economical solution. In one implementation, the access control system 300 may allow an enterprise customer to optionally choose between one or a combination of the biometric scanner 304, the keypad 120 (as described above with reference to FIG. 1), or the RFID card reader (as described above with reference to FIG. 1).

Blocks 322-332 further describe the operations in the access control system 300. For example, these operations may be performed by one or more hardware components of the system separately, and/or in conjunction with, the processor 103 executing computer-readable instructions stored in the storage device 101. At block 322, the biometric identification unit 302 may send temperature reading(s) of the user (as described above) to the processor 103 of the access control system 300 over a network interface (e.g., over a Wiegand interface using Wiegand protocol). At block 324, the processor 103 or a controller of the access control system 300 may receive the data including temperature reading(s) of the user. The processor 103 may transfer/send the data may to one or more devices of the access control system 300 via a communication network of the access control system 300 (e.g., using transmission control protocol (TCP)/internet protocol (IP) (TCP/IP). At block 326, a dedicated system (e.g., a record logging unit of the access control system 300) may record the data. Also, an operator or a security officer may record the data into the dedicated system. At block 328, the processor 103 of the access control system 300 may compare the temperature reading(s) of the user against a threshold temperature value or a range of temperature values. In one implementation, on determining that the temperature reading(s) of the user is below the threshold temperature value, the processor 103 may send instructions to a door lock controller to unlock a door to allow the source 102 access to the secured area. In another implementation, on determining that the temperature reading(s) of the user falls outside the range of temperature values, the processor 103 may send instructions to the door lock controller to unlock the door to allow the source 102 access to the secured area. The processor 103 may instruct the door lock controller to keep the door in a locked state when the temperature reading(s) of the user are above the threshold temperature value and/or outside the range of temperature values. Further, the processor 103 may log the temperature values in an Alarm/Log Report (as described above).

At block 330, the processor 103 may send alerts (including details of an identified user as described above) to a security officer and other public health departments when the temperature reading(s) of the user are above the threshold temperature value and/or within the range of temperature values. At block 332, the output data may be utilized by one or more security officers/public health agencies to track, trace and/or limit mobility of the user.

Figure 4:
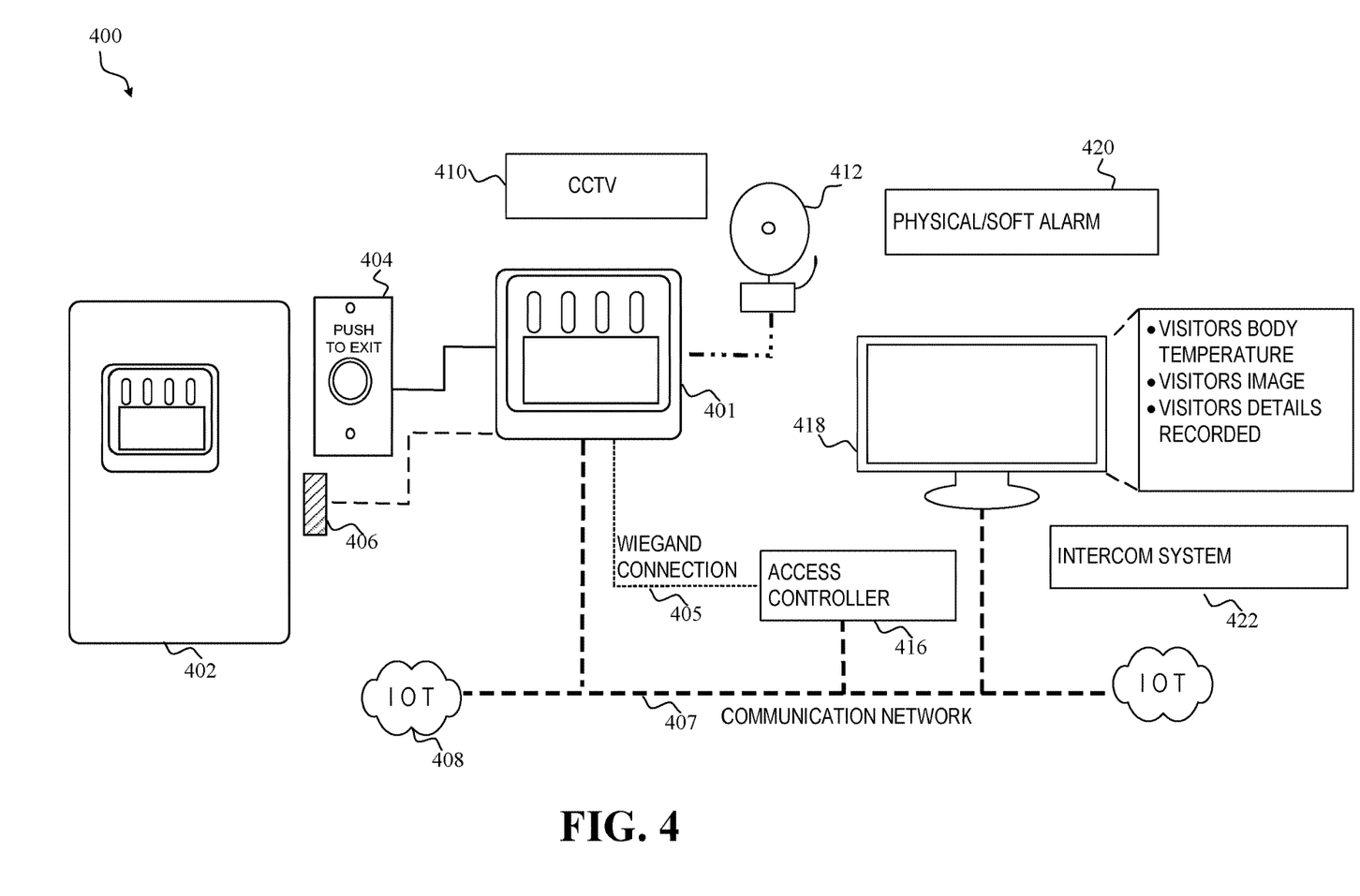
FIG. 4 is a high level diagram of system components of an access control system with additional safety features.

Referring to FIG. 4, a system architecture diagram 400 of the access control system 300 (as described above with reference to FIG. 3), includes an access control door 402 that may provide a controlled access to the source 102. The operations described with respect to FIG. 4 may be performed by one or more hardware components of the system separately, and/or in conjunction with, the processor 103 executing computer-readable instructions stored in the storage device 101. The access control door 402 may include the biometric identification unit 302 (as described above with reference to FIG. 3) to allow a user trying to gain access to the controlled area to interact with the access control system 300 and present the credentials of the user. In one implementation, the access control door 402 may include a biometric scanner 401 (similar to the biometric scanner 304 as described above in FIG. 3). The biometric scanner 401 may include the IR transmitter LED and the IR detector 108 (as described above in FIG. 1) for obtaining temperature reading(s) of a user. The biometric scanner 401 may be coupled to an access controller 416 via a Wiegand interface/connection 405. The biometric scanner 401 and the access controller 416 may be coupled to one or more internet of things (IOT) devices 408 such as an emergency alert system, one or more servers of public health departments, etc. via a communication network 407 of the access control system 300. The access controller 416 may perform some or all operations of the processor 103 of the access control system 300 (as described above in FIGS. 1 and 3). The system architecture diagram 400 may include a request to exit button 404 that may allow a user to request exit in case of an unsuccessful authentication.

The system architecture diagram 400 may also include a close circuit television (CCTV) camera 410 (similar to the camera 112 as described above in FIGS. 1 and 3) and an electric door lock 406 that may be selectively unlocked based on instructions received from the access controller 416 (based on determination of the temperature reading(s) of the user as described above in FIGS. 1 and 3). The access controller 416 may be coupled to an access control component 418 (which may include access control software, firmware, and/or hardware components) to perform the operations as described above in FIGS. 1 and 3. The access controller 416 may also be coupled to a local alarm 412 to immediately alert a security officer managing the secured area when the temperature reading(s) of the user are above the threshold temperature value and/or outside the range of temperature values (as described above in FIG. 1). The access control component 418 may maintain information logs about the user trying to gain access to the secured area such as a body temperature of the user, an image of the user captured through the access control component 418. The access control component 418 may include a physical/soft alarm 420 that may be triggered when the temperature reading(s) of the user are above the threshold temperature value and/or outside the range of temperature values. Based on the triggering of the physical/soft alarm 420, the access controller 416 may perform one or more operations such as update entries in an Alarm/Log Report. The access controller 416 may be coupled to an intercom system 422 to call a security officer when the physical/soft alarm 420 is triggered.

Figure 5:
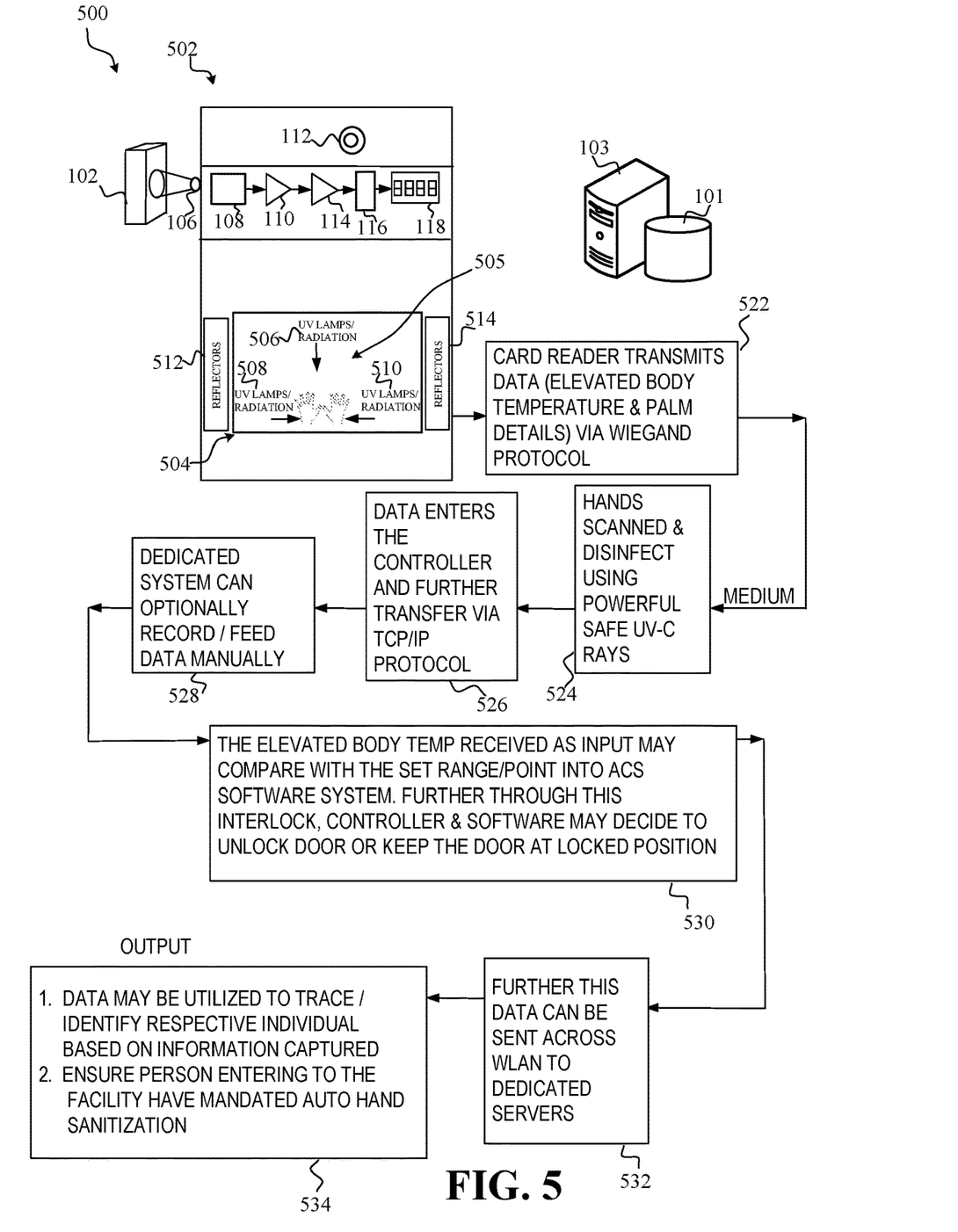
FIG. 5 is a block diagram of a third implementation of an access control system with additional safety features.

Referring to FIG. 5, an access control system 500 includes similar entities as the access control system 100 in FIG. 1 with the biometric identification unit 502 in place of the source reader 104. The biometric identification unit 502 includes the LED component 106, the IR detector 108, the amplifier 110, the signal conditioner 114, the ADC converter 116 and the display 118 (as described above in FIG. 1). The biometric identification unit 502 includes a palm scanner and sanitization unit 504 to scan one or both palms of a user trying to gain access to a secured area. The palm scanner and sanitization unit 504 includes ultraviolet (UV) lamps 506, 508 and 510 that may emit UV light from three directions. The palm scanner and sanitization unit 504 is not limited to having only three UV lamps, but the palm scanner and sanitization unit 504 may include four or more UV lamps to provide UV light from all directions. The palm scanner and sanitization unit 504 may also include reflectors 512 and 514 on the outside boundary walls of the UV lamps 508 and 510, respectively. The reflectors 512 and 514 reflect back the UV light into a palm placement area 505 of the palm scanner and sanitization unit 504. The palm placement area 505 of the palm scanner and sanitization unit 504 may also include one or more biometric readers (e.g., a fingerprint reader, a palm reader, etc.) to capture biometric data of a user who places their palms in the palm placement area 505. The biometric identification unit 502 may communicate the biometric data of the user received to a processor 103 of the access control system 500. The processor 103 may compare the biometric data of the user received from the biometric identification unit 502 against one or more allowed user biometric identifiers stored in a storage of the access control system 500 to determine whether the user trying to gain access should be granted access. In one implementation, the palm scanner and sanitization unit 504 may not include biometric readers, and identification data of the user may be captured using another biometric reader (e.g., an iris scanner as described above with reference to FIG. 3), or an RFID card reader, or a keypad (as described above with reference to FIG. 1).

The biometric identification unit 502 may include the LED component 106 (as described above in FIG. 1) having an IR transmitter LED that may act as a source of IR radiation. The biometric identification unit 502 may include the IR detector 108 (as described above in FIG. 1) e.g., an IR receiver which may be a photodiode to detect the IR radiation. In one implementation, the IR transmitter LED and the IR detector 108 may be integrated into the palm scanner and sanitization unit 504. In one implementation, the IR transmitter may be positioned towards the palm placement area 505 in such a manner that the transmitted IR radiation is focused on the palm of the user attempting to gain access to the secured area. The IR transmitter may emit rays on the palm of the user at the time of attempting access to the secured area. In another implementation, the IR transmitter may be positioned towards one or more body parts of the user (e.g., forehead of the user) instead of being positioned towards the palm placement area 505. The IR detector 108 may detect the reflected IR radiation from the body parts of the user which may be amplified by an amplifier 110. The signal conditioner 114 may process (e.g., by amplifying, filtering and/or attenuating) the amplified signals received from the amplifier 110 for processing by the ADC converter 116. The ADC converter 116 may convert the received signals to digital signals suitable to be processed by one or more components of the access control system 500 to obtain temperature reading(s) of the user trying to gain access to the secured area.

A storage device 101 of the access control system 500 may store the temperature reading(s) of the user may. The temperature reading(s) of the user may be flashed on to an Alarm/Log Report list of the access control system 500. For example, the processor 103 of the access control system 500 may flash the temperature reading(s) of the user on the Alarm/Log Report list when the temperature reading(s) of the user are greater than a threshold (e.g., 99.4 degrees Fahrenheit). Further, the processor 103 of the access control system 500 may classify the temperature reading(s) of the user may on the Alarm/Log Report list in a different color (e.g., green) when the temperature reading(s) of the user are below the threshold, and the processor 103 of the access control system 500 may classify temperature reading(s) of the user on the Alarm/Log Report list in a different color (e.g., red) when the temperature reading(s) of the user are above the threshold.

A security management system of the access control system 500 may provide the data (such as red classified entries in the Alarm/Log Report list) to a log alarm report. The security management system may be defined by instructions executed by the processor 103, and the log alarm report may be stored in the storage device 101. The display 118 may display a pop-up when the temperature of the user captured is above a threshold. Further, the processor 103 of the access control system 500 may send instructions to sound an audible alarm along with displaying the pop-up on the display 118. The camera 112 may be connected to a storage device of the access control system 500 communication network and capture an image(s) and/or video of the person trying to gain access to the secured area. The image(s) and/or video captured by the camera 112 of the person may be compared against one or more identifying pictures of users stored in the storage of the access control system 500. On identifying the person based on such comparison and/or using the identification details received from the biometric identification unit 502, the processor 103 of the access control system 500 may alert a security officer about other details of the person such as: name, contact numbers, addresses, etc. The processor 103 may further send such details to state municipal departments, health departments, traffic signal departments or state police departments in case of a pandemic scenario via the communication network of the access control system 500. Such data may enable limiting, tracing or tracking the movements of the user.

The palm scanner and sanitization unit 504 may sanitize one or both hands of the user trying to gain access to the secured area. In one implementation, the UV lamps 508 and 510 may emit UV-C rays which may have a wavelength such that the light energy in the UV-C rays may be converted into dissipated heat energy which may be transferred into palm placement area 505 and targeted on the palm(s) of the user. The power and wavelength of the UV-C rays are chosen such that they are safe for a user's body and lethal to one or more microorganisms desired to be eliminated. For example, generic bacteria, fungus or viruses may be killed in a temperature range of 140-170 degrees Fahrenheit.

Blocks 522-534 further describe the operations in the access control system 500. For example, these operations may be performed by one or more hardware components of the system separately, and/or in conjunction with, the processor 103 executing computer-readable instructions stored in the storage device 101. At block 522, the biometric identification unit 502 may send temperature reading(s) of the user (as described above) to the processor 103 of the access control system 500 over network interface (e.g., over a Wiegand interface using Wiegand protocol). At block 524, the processor 103 of the access control system 500 may instruct the palm scanner and sanitization unit 504 to scan and sanitize the hands of the user (as described above) using UV-C rays.

At block 526, the processor 103 of the access control system 500 may classify data including temperature reading(s) of the user. The processor 103 may transfer/send the data may to one or more devices of the access control system 500 via a communication network of the access control system 500 (e.g., using transmission control protocol (TCP)/internet protocol (IP) (TCP/IP). At block 528, a dedicated system (e.g., a record logging unit of the access control system 500) may record the data. Also, an operator or a security officer may record the data into the dedicated system. At block 530, the processor 103 of the access control system 500 may compare the temperature reading(s) of the user against a threshold temperature value or a range of temperature values. In one implementation, on determining that the temperature reading(s) of the user is below the threshold temperature value, the processor 103 may send instructions to a door lock controller to unlock a door to allow the source 102 access to the secured area. In another implementation, on determining that the temperature reading(s) of the user falls outside the range of temperature values, the processor 103 may send instructions to the door lock controller to unlock the door to allow the source 102 access to the secured area. The processor 103 may instruct the door lock controller to keep the door in a locked state when the temperature reading(s) of the user are above the threshold temperature value and/or outside the range of temperature values. Further, the processor 103 may log the temperature values in an Alarm/Log Report (as described above).

At block 532, the processor 103 may send alerts (including details of an identified user as described above) to a security officer and other public health departments when the temperature reading(s) of the user are above the threshold temperature value and/or within the range of temperature values. At block 534, the output data may be utilized by one or more security officers/public health agencies to track, trace and/or limit mobility of the user. The access control system 500 enables auto hand sanitization for a user before the user is granted access to the secured area.

Figure 6:
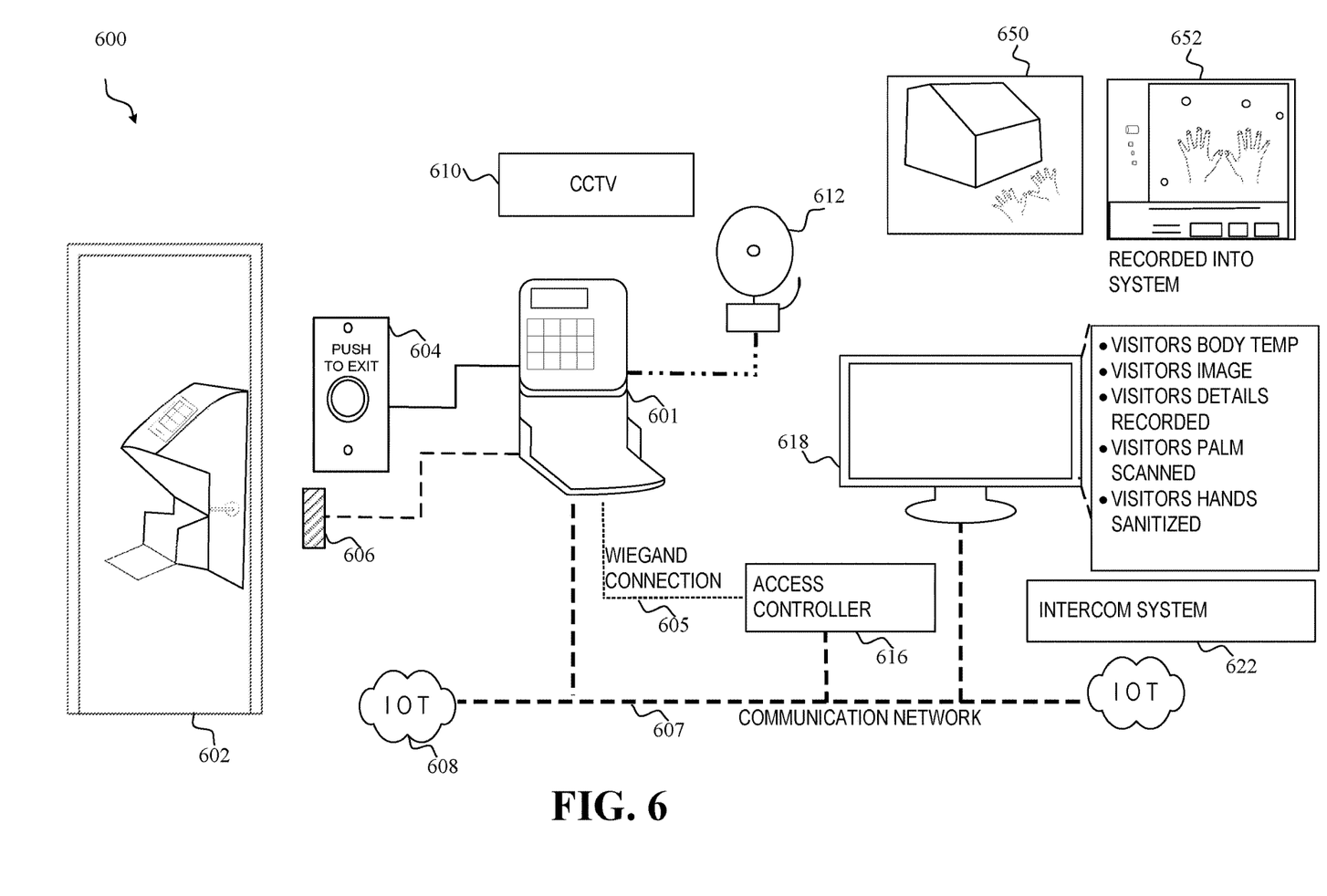
FIG. 6 is a high level diagram of system components of an access control system with additional safety features.

Referring to FIG. 6, a system architecture diagram 600 of the access control system 500 (as described above with reference to FIG. 5), includes an access control door 602. The operations described with respect to FIG. 6 may be performed by one or more hardware components of the system separately, and/or in conjunction with, the processor 103 executing computer-readable instructions stored in the storage device 101. The access control door 602 may include a biometric palm card reader 601 (similar to the biometric identification unit 502 as described above with reference to FIG. 5) to allow a user trying to gain access to the controlled area to interact with the access control system 500 and present the credentials of the user. The biometric palm card reader 601 may include the IR transmitter LED and the IR detector 108 (as described above in FIGS. 1 and 5) for obtaining temperature reading(s) of a user. The biometric palm card reader 601 may be coupled to an access controller 616 via a Wiegand interface/connection 605. The biometric palm card reader 601 and the access controller 616 may be coupled to one or more internet of things (IOT) devices 608 such as an emergency alert system, one or more servers of public health departments, etc. via a communication network 607 of the access control system 500. The access controller 616 may perform some or all operations of the processor 103 of the access control system 500 (as described above in FIGS. 1 and 5). The system architecture diagram 600 may include a request to exit button 604 that may allow a user to request exit in case of an unsuccessful authentication.

The system architecture diagram 600 may also include a close circuit television (CCTV) camera 610 (similar to the camera 112 as described above in FIGS. 1 and 5) and an electric door lock 606 that may be selectively unlocked based on instructions received from the access controller 616 (based on determination of the temperature reading(s) of the user as described above in FIGS. 1 and 5). The access controller 616 may be coupled to an access control component 618 (which may include access control software, firmware, and/or hardware components) to perform the operations as described above in FIGS. 1 and 5. The access controller 616 may also be coupled to a local alarm 612 to immediately alert a security officer managing the secured area when the temperature reading(s) of the user are above the threshold temperature value and/or outside the range of temperature values (as described above in FIG. 1). The access control component 618 may maintain information logs about the user trying to gain access to the secured area such as a body temperature of the user, an image of the user captured through the access control component 618 and may include a physical/soft alarm that may be triggered when the temperature reading(s) of the user are above the threshold temperature value and/or outside the range of temperature values. Based on the triggering of the physical/soft alarm, the access controller 616 may perform one or more operations such as update entries in an Alarm/Log Report. The access controller 616 may be coupled to an intercom system 622 to call a security officer when the physical/soft alarm is triggered. The access control component 618 may also maintain logs of the duration for which the hands of the user were sanitized. In one implementation, the access control component 618 may raise an alarm to the user if the user removes the hands before the hand sanitization process is complete. Hand sanitization process as achieved by the access control system 500 is illustrated through blocks 650 and 652.

Figure 7:
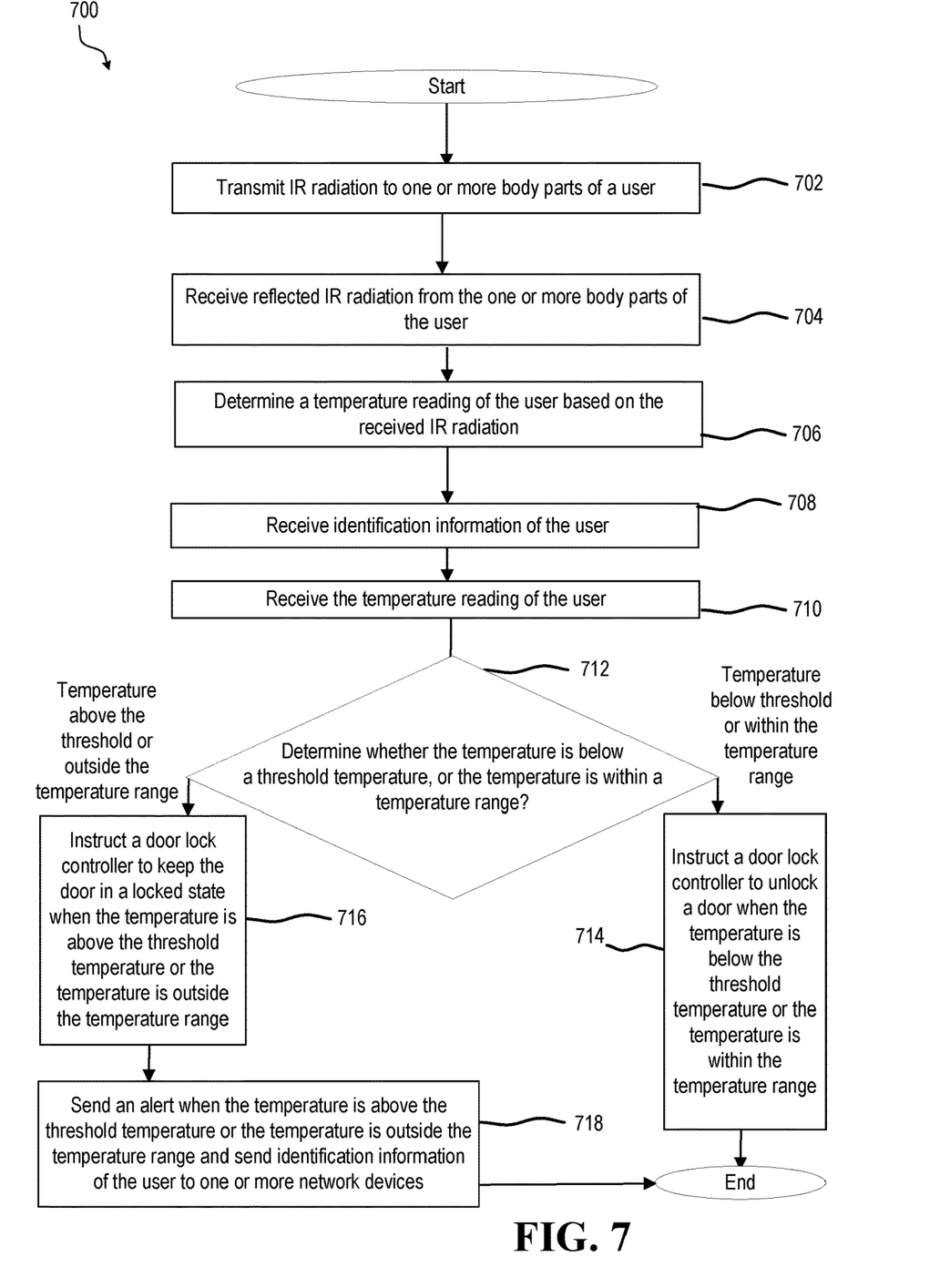
FIG. 7 is a flow diagram of example operations of the access control system with additional safety features.

FIG. 7 is a flowchart 700 of a method of managing access to a secured area (as described above with reference to FIGS. 1-4). The operations of the below described methods may be performed by the processor 103 based on executing instructions stored in a memory, such as the storage device 101 (as described above with reference to FIGS. 1-4).

At block 702, the method transmits IR radiation to one or more body parts of a user. In one implementation, the IR transmitter LED of the LED component 106 transmits the IR radiation. For example, the processor 103 may execute one or more instructions causing the transmitter LED to transmit the IR radiation.

At block 704, the method receives reflected IR radiation from the one or more body parts of the user. In one implementation, the IR detector 108 receives the reflected IR radiation. For example, the processor 103 may execute one or more instructions causing the IR detector 108 to capture the IR radiation.

At block 706, the method determines a temperature reading of the user based on the received reflected IR radiation. In one implementation, one or more signal processing components of the source reader 104 (as described above with reference to FIG. 1) determine a temperature reading of the user based on the received reflected IR radiation. In another implementation, one or one or more components of the biometric identification unit 302 (as described above with reference to FIG. 3) determine a temperature reading of the user based on the received reflected IR radiation. For example, the processor 103 may execute one or more instructions causing the signal processing components (of the source reader 104 or the biometric identification unit 302) to process/convert the received reflected IR radiation to digital temperature readings.

At block 708, the method receives identification information of the user. In one implementation, the keypad 120 or an RFID card reader receives the identification information of the user (e.g., using a keycode or an embedded code in an RFID card). In another implementation, the biometric scanner 304 receives the identification information of the user (e.g., an iris scan of the user). For example, the processor 103 may execute one or more instructions causing the keypad 120/the RFID card reader/the biometric scanner 304 to receive the identification information.

At block 710, the method receives the temperature reading of the user. In one implementation, the processor 103 receives the temperature reading of the user from the source reader 104. In another implementation, the processor 103 receives the temperature reading of the user from the biometric identification unit 302. For example, the processor 103 may receive the temperature reading of the user from the source reader 104 or the biometric identification unit over a Wiegand interface using Wiegand protocol.

At block 712, the method determines whether the temperature is below a threshold temperature, or the temperature is within a temperature range. In one implementation, the processor 103 determines whether the temperature reading (received at block 710) is below the threshold temperature (e.g., 37.5 degrees Celsius (99.5 degrees Fahrenheit)). In another implementation, the processor 103 determines whether the temperature reading (received at block 710) is within the temperature range (e.g., between 36.5 degrees Celsius (97.7 degrees Fahrenheit) and 37.5 degrees Celsius (99.5 degrees Fahrenheit)). If the processor 103 determines whether the temperature is below the threshold temperature or within the temperature range, the method performs operations at block 714. If the processor 103 determines that the temperature is above the threshold temperature or outside the temperature range, the method performs operations at block 716.

At block 714, the method instructs a door lock controller to unlock a door when the temperature is below the threshold temperature or the temperature is within the temperature range. In one implementation, the processor 103 executes instructions causing the access controller 216 (as described above with reference to FIG. 2) to unlock the electric door lock 206. In another implementation, the processor 103 executes instructions causing the access controller 416 (as described above with reference to FIG. 4) to unlock the electric door lock 406.

At block 716, the method instructs a door lock controller to keep the door in a locked state when the temperature is above the threshold temperature or the temperature is outside the temperature range. In one implementation, the processor 103 executes instructions causing the access controller 216 (as described above with reference to FIG. 2) to keep the electric door lock 206 in the locked state. In another implementation, the processor 103 executes instructions causing the access controller 416 (as described above with reference to FIG. 4) to keep the electric door lock 406 in the locked state. After block 716, the method performs operations at block 718.

At block 718, the method sends an alert when the temperature is above the threshold temperature or the temperature is outside the temperature range and send identification information of the user to one or more network devices. In one implementation, the processor 103 executes instructions to send alerts (including identification details of the identified user) to a security officer and/or other public health departments.

As used herein, an element or step recited in the singular and proceeded with the word "a" or "an" should be understood as not excluding plural elements or steps, unless such exclusion is explicitly recited. Furthermore, references to "one embodiment" are not intended to be interpreted as excluding the existence of additional embodiments that also incorporate the recited features.

The various embodiments or components described above, for example, access control system and the components or processors therein, may be implemented as part of one or more computer systems. Such a computer system may include a computer, an input device, a display unit and an interface, for example, for accessing the Internet. The computer may include a microprocessor. The microprocessor may be connected to a communication bus. The computer may also include memories. The memories may include Random Access Memory (RAM) and Read Only Memory (ROM). The computer system further may include a storage device, which may be a hard disk drive or a removable storage drive such as a floppy disk drive, optical disk drive, and the like. The storage device may also be other similar means for loading computer programs or other instructions into the computer system. As used herein, the term "software" includes any computer program stored in memory for execution by a computer, such memory including RAM memory, ROM memory, EPROM memory, EEPROM memory, and non-volatile RAM (NVRAM) memory. The above memory types are exemplary only, and are thus not limiting as to the types of memory usable for storage of a computer program.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. An access control system for managing access to a secured area, comprising:
    an identification unit, including:
        an infrared (IR) transmitter configured to transmit IR radiation to one or more body parts of a user;
        an IR detector configured to receive reflected IR radiation from the one or more body parts of the user;
        one or more signal processing components to determine a temperature reading of the user based on the reflected IR radiation;
        an identification device to receive identification information of the user, the identification information corresponding to the one or more body parts of the user; and
    a processor configured to:
        receive the temperature reading of the user;
        determine whether the temperature reading is within a temperature range with a lower limit value of 36.5 degrees Celsius (97.7 degrees Fahrenheit) and an upper limit value of 37.5 degrees Celsius (99.5 degrees Fahrenheit);
        instruct a door lock controller to unlock a door when the temperature is below a threshold temperature or the temperature is within the temperature range;
        instruct a sanitization unit to sanitize a body part when the temperature reading is below the threshold temperature or the temperature is within the temperature range;
        instruct a door lock controller to keep the door in a locked state when the temperature reading is above the threshold temperature or the temperature reading is outside the temperature range; and
        send an alert when the temperature reading is above the threshold temperature or the temperature reading is outside the temperature range and send identification information of the user to one or more network devices.

2. The access control system of claim 1, wherein the identification device comprises one or a combination of:
    a keypad;
    a radio frequency identification (RFID) reader; or
    a biometric scanner.

3. The access control system of claim 2, wherein the biometric scanner comprises one or a combination of:
    an iris scanner;
    a fingerprint scanner; or
    a palm scanner.

4. The access control system of claim 1, wherein the access control system includes a compatible interface for on-top integration with one or more legacy access control systems.

5. The access control system of claim 1, wherein the processor is further configured to generate a log alarm report, the log alarm report comprising identifiable entries corresponding to temperature above the threshold temperature.

6. The access control system of claim 1, wherein to send the alert further comprises one or a combination of:
    the processor is further configured to send an alert to a security officer managing the secured area; or
    the processor is further configured to trigger an alarm.

7. A method for managing access to a secured area, comprising:
    transmitting IR radiation to one or more body parts of a user;
    receiving reflected IR radiation from the one or more body parts of the user;
    determining a temperature reading of the user based on the reflected IR radiation;
    receiving identification information of the user, the identification information corresponding to the one or more body parts of the user;
    receiving the temperature reading of the user;
    determining whether the temperature reading is within a temperature range with a lower limit value of 36.5 degrees Celsius (97.7 degrees Fahrenheit) and an upper limit value of 37.5 degrees Celsius (99.5 degrees Fahrenheit);
    instructing a door lock controller to unlock a door when the temperature reading is below a threshold temperature or the temperature reading is within the temperature range;
    instructing a sanitization unit to sanitize the body part when the temperature reading is below the threshold temperature or the temperature reading is within the temperature range;
    instructing a door lock controller to keep the door in a locked state when the temperature reading is above the threshold temperature or the temperature reading is outside the temperature range; and
    sending an alert when the temperature reading is above the threshold temperature or the temperature reading is outside the temperature range and send identification information of the user to one or more network devices.

8. The method of claim 7, wherein the identification information of the user comprises one or a combination of:
    a keycode;
    a radio frequency identification (RFID) code; or
    biometric data.

9. The method of claim 8, wherein the biometric data comprises one or a combination of:
    an iris scan;
    a fingerprint scan; or
    a palm scan.

10. The method of claim 7, further comprising:
    generating a log alarm report, the log alarm report comprising identifiable entries corresponding to temperature above the threshold temperature.

11. The method of claim 7, wherein the sending the alert further comprises one or a combination of:
sending an alert to a security officer managing the secured area; or
triggering an alarm.

12. A non-transitory computer readable medium for managing access to a secured area, the non-transitory computer readable medium having instructions thereon that, when executed by at least one computing device, causes the at least one computing device to perform operations comprising:
transmitting IR radiation to one or more body parts of a user;
receiving reflected IR radiation from the one or more body parts of the user;
determining a temperature reading of the user based on the reflected IR radiation;
receiving identification information of the user, the identification information corresponding to the one or more body parts of the user;
receiving the temperature reading of the user;
determining that the temperature reading is within a temperature range with a lower limit value of 36.5 degrees Celsius (97.7 degrees Fahrenheit) and an upper limit value of 37.5 degrees Celsius (99.5 degrees Fahrenheit);
instructing a door lock controller to unlock a door when the temperature reading is below a threshold temperature or the temperature reading is within the temperature range;
instructing a sanitization unit to sanitize the one or more body parts when the temperature reading is below the threshold temperature or the temperature reading is within the temperature range;
instructing a door lock controller to keep the door in a locked state when the temperature reading is above the threshold temperature or the temperature reading is outside the temperature range; and
sending an alert when the temperature reading is above the threshold temperature or the temperature reading is outside the temperature range and send identification information of the user to one or more network devices.

13. The non-transitory computer readable medium of claim 12, the operations further comprising:
generating a log alarm report, the log alarm report comprising identifiable entries corresponding to temperature above the threshold temperature.

14. The non-transitory computer readable medium of claim 12, wherein the sending the alert further comprises one or a combination of:
sending an alert to a security officer managing the secured area; or
triggering an alarm.

* * * * *